(12) United States Patent
Thompson et al.

(10) Patent No.: US 7,162,933 B2
(45) Date of Patent: Jan. 16, 2007

(54) GAS SAMPLE CONDITIONING SYSTEM

(75) Inventors: Kenneth O Thompson, Ravenswood, WV (US); Walter F. Gerhold, Sherman, WV (US)

(73) Assignee: Valtronics, Inc., Murrayville, WV (US)

( * ) Notice: Subject to any disclaimer, the term of this patent is extended or adjusted under 35 U.S.C. 154(b) by 0 days.

(21) Appl. No.: 11/169,619

(22) Filed: Jun. 30, 2005

(65) Prior Publication Data

US 2006/0000298 A1    Jan. 5, 2006

Related U.S. Application Data

(60) Provisional application No. 60/583,792, filed on Jun. 30, 2004.

(51) Int. Cl.
*G01N 1/22*    (2006.01)
(52) U.S. Cl. .................................. 73/863.11
(58) Field of Classification Search .............. 73/863.11
See application file for complete search history.

(56) References Cited

U.S. PATENT DOCUMENTS

| | | | | |
|---|---|---|---|---|
| 3,793,887 A | * | 2/1974 | Anderson et al. ........ | 73/863.03 |
| 3,976,450 A | * | 8/1976 | Marcote et al. .............. | 96/12 |
| 4,296,637 A | * | 10/1981 | Calamur et al. ......... | 73/863.11 |
| 5,109,711 A | * | 5/1992 | Wendt ..................... | 73/863.11 |
| 5,321,984 A | * | 6/1994 | Stroupe .................... | 73/863.11 |
| 5,544,276 A | * | 8/1996 | Loux et al. ................. | 392/480 |
| 6,022,510 A | * | 2/2000 | Springmann ................. | 422/101 |
| 6,114,178 A | * | 9/2000 | Dezael et al. ............... | 436/180 |
| 6,539,312 B1 | * | 3/2003 | Nimberger et al. ........... | 702/24 |
| 2001/0049973 A1 | * | 12/2001 | Hanashiro et al. ........ | 73/863.11 |

FOREIGN PATENT DOCUMENTS

GB    2158608    * 11/1985

* cited by examiner

*Primary Examiner*—Robert Raevis
(74) *Attorney, Agent, or Firm*—Cahn & Samuels, LLP.

(57) ABSTRACT

A gas sample and conditioning device for sampling gas in a storage or transport device and conditioning the gas to avoid dew point dropout of the gas. A chamber for regulating the temperature and the pressure of the gas is provided with external A.C. or D.C. power using the leads of existing heat tracing cables to avoid the need for additional power sources to power the temperature and pressure regulating devices within the chamber.

9 Claims, 4 Drawing Sheets

GAS SAMPLE CONDITIONING SYSTEM

CROSS REFERENCE TO RELATED APPLICATIONS

This application is an application filed under 35 U.S.C. § 111(a) claiming benefit pursuant to 35 U.S.C. § 119(e)(1) of Provisional Application Ser. No. 60/583,792, filed on Jun. 30, 2004, pursuant to 35 U.S.C. § 111(b), the entire content of which is incorporated herein by reference.

FIELD OF THE INVENTION

This invention relates generally to collecting and conditioning samples of compositions in gaseous form. More particularly, the invention relates to thermal conditioning of pipeline samples from natural gas pipelines.

BACKGROUND OF THE INVENTION

Natural gas is a combustible, gaseous mixture of several different hydrocarbon compounds and is typically extracted from deep underground reservoirs formed by porous rock. The composition of natural gas extracted from different reservoirs varies depending on the geographic location of the reservoir. In fact, it is not entirely uncommon for the composition of gas extracted from a single given reservoir to vary to an extent. Regardless of any variations, however, the primary component of natural gas is methane, a colorless, odorless, gaseous saturated hydrocarbon. Methane usually makes up from 80% to 95% of any natural gas sample and the balance is composed of varying amounts of ethane, propane, butane, pentane and other hydrocarbon compounds.

Natural gas is used extensively in residential, commercial and industrial applications. It is the dominant energy used for home heating with well over half of American homes using natural gas. The use of natural gas is also rapidly increasing in electric power generation and cooling, and as a transportation fuel.

Natural gas, like other forms of heat energy, is measured in British thermal units or Btu. One Btu is equivalent to the heat needed to raise the temperature of one pound of water by one degree Fahrenheit at atmosphere pressure.

A cubic foot of natural gas has about 1,027 Btu. Natural gas is normally sold from the wellhead, i.e., the point at which the gas is extracted from the earth, to purchasers in standard volume measurements of thousands of cubic feet (Mcf). However, consumer bills are usually measured in heat content or therms. One therm is a unit of heating equal to 100,000 Btu.

Three separate and often independent segments of the natural gas industry are involved in delivering natural gas from the wellhead to the consumer. Production companies explore, drill and extract natural gas from the ground; transmission companies operate the pipelines that connect the gas fields to major consuming areas; and distribution companies are the local utilities that deliver natural gas to the customer.

In the United States alone, natural gas is delivered to close to 200 million consumers through a network of underground pipes that extends over a million miles. To produce and deliver this natural gas there are over a quarter-million producing natural gas wells, over one hundred natural gas pipeline companies and more than a thousand local distribution companies (LDCs) that provide gas service to all 50 states.

Prior to regulatory reform, which essentially restructured the industry, producers sold gas to the pipeline companies, who sold it to the LDCs, who sold it to residential and other customers. Post-regulation, however, pipeline companies no longer purchase gas for resale. Instead, the pipeline companies merely transport gas from sellers, such as producers or marketers, to buyers, such as electric utilities, factories and LDCs. Thus, the LDCs now can choose among a variety of sellers of natural gas, whereas before they could only buy gas from one source, i.e., the pipeline company. Further, some states have implemented additional restructuring which renders the LDCs subject to regulation by State public utility commissions. Prior to these additional state regulations, an LDC's residential customers could only buy gas from one source, i.e., the LDC. After state regulation, however, residential customers can choose a different supplier other than their LDC from which to buy the gas. The consumer's LDC, as the owner/operator of the distribution network, delivers the gas to the consumer, as before, but the LDC only charges the consumer for delivery of the gas and the independent supplier bills for the gas.

As a result, sampling and analysis of the natural gas along various points in the pipeline network has become an increasingly more important endeavour. More particularly, because consumers are typically billed for natural gas in Btu's, it is important that the Btu measurement of any particular gas volume be accurate. Further, because various suppliers can, and do, supply their respective gas, which comes from widely varying geographic locations, to the single network of pipelines, the measured Btu value within a given section of pipe will vary.

According to the current state of the art in gas sample conditioning, gas samples are extracted via a probe from a gas pipeline by using a so-called insertion probe. Once the gas sample is extracted, it is typically provided through stainless steel tubing with a relatively small diameter to an analyzer, such a, a chromatograph, for analysis. A chromatograph is a device that utilizes a family of analytical chemistry techniques to separate mixtures into their constituent components. Typically, the techniques utilized by a chromatograph include separating the components of the mixture on the basis of differences in their affinity for a stationary and a mobile phase.

The distance between the gas line and the analyzer often exceeds thirty (30) feet and may even exceed one-hundred (100) feet. Across this length, the gas sample moves from a zone of high pressure at the probe, e.g., 2000 psig, to a relatively low pressure zone, e.g., 10–30 psig, the preferred pressure for a typical analyzer/chromatograph. Due to this rather substantial decrease in pressure, also known as adiabatic compression, the gas sample is cooled, toward its freezing point. If the gas sample temperature decreases below the gas dew point, condensation occurs. This phenomenon is known as hydrocarbon dew point dropout.

When this happens, the analyzer/chromatograph can potentially be seriously damaged because chromatograph devices ideally operate on dry input gases. When a chromatograph is damaged in this manner it must be taken offline in order to perform the repair. This downtime results in higher costs and inaccurate measurements. Accordingly, it is increasingly more important to maintain the gas being sampled at a constant temperature in order to reduce the chances of hydrocarbon dew point dropout in the sampled gas.

The issue of hydrocarbon dew point dropout in gas sampling has been addressed by heating the sample gases, as well as the pressure regulators, gas lines, and other components, that come into contact with the sample gas, between the pipeline and the analyzer/chromatograph to keep the temperature of the gas above its dew point, thus preventing any of the gas being sampled from entering its liquid.

Natural gas sampling systems, however, are typically located in harsh environments, e.g., where outdoor ambient temperatures can be significantly below the gas dew point temperature and where dangerous explosion-prone gas vapors are often permeating into the surrounding atmosphere. Accordingly, the heating mechanism used must adhere to strict standards in order to generate enough heat to overcome the low ambient temperature and do so without exposing the dangerous hydrocarbon gases in the atmosphere to any safety problems, such as electrical wiring, etc.

For example, the American Petroleum Institute (API) has suggested heating the sample probe and using heat tracing lines to heat the gas line between the probe and the analyzer. Such systems often rely on catalytic heaters to maintain temperature stability and avoid undesirable temperature changes to the gas sample communicated between a source, e.g., pipeline and the analyzer. Catalytic heaters of the type referred to by the API in its Manual of Petroleum Standards call for heating a sample gas stream throughout a selected portion of a system where the heated sample is then introduced into a heated tube bundle of the analyzer.

Several problems are known to exist with prior art gas sample heating systems. For example, in the case where a heater system employs electrical initiation, in order to ignite the heaters when they are used in the field, these related art systems typically rely on the use of relatively large batteries, (e.g., 12V batteries similar to those used in an automobile). Obviously, exposing the hydrocarbon vapors in and around the sampling system to a spark potentially created by 12 volt car battery is not a desirable situation, e.g., due to the high risk of explosion.

Other related art systems, e.g., catalytic heaters adapted to operate by burning stored natural gas, are not economical and suffer from an increased operating expense, particularly under present market conditions. Another, perhaps more significant, issue with conventional sample heater systems is the failure rate of such systems. Because failure rates of typical conventional systems are at unacceptably high levels, the reliability of the sample testing systems have become problematic.

Some systems have been developed in an attempt to address the foregoing concerns regarding conventional gas sampling systems. For example, PGI International, of Houston, Tex., has produced a gas-sampler called the "Hot-Shot" that features a catalytic heater enclosed in an insulated stainless steel cabinet. The catalytic heater in the "Hot-Shot" utilizes infrared heat to maintain the gas sampling components at a temperature between 100 degrees and 140 degrees F.

Another known system, the High Pressure Gas Sampling System, Model 2020, produced by Tekran Inc., of Toronto, Canada, is illustrated in FIG. 7. The Tekran system includes an electrically heated pressure regulator for eliminating, sample condensation during pressure reduction. As shown, the system of FIG. 9 accepts natural gas at an inlet pressure of 50–2000 PSI before passing the gas through valves, vents, the pressure regulator, gauges and a manual injection port, before releasing the gas at an adjustable outlet pressure of between 0 and 30 PSI. The Tekran system, however, requires that an external 110–125 volt A.C. power supply be provided to provide heat to the heated regulator.

Another known system is described in U.S. Pat. No. 5,611,846, to Overton et al. Overton et al. discloses a portable gas chromatograph that operates at 100 watts peak power, 12 V DC, supplied to the unit from a power pack or other DC source; the power pack supplies 140 watt-hrs of uninterrupted power at 12 V DC.

Other conventional systems not necessarily associated with gas sampling in hazardous environments have also been suggested. For example, certain systems related to the medical arts describe the use of heated pressure regulators for controlling pressure, flow rate, and temperature of a gas being administered to a patient. There exists, however, a need for improvement to the presently accepted and commonly used systems and methods of heating gas samples in the field.

SUMMARY OF THE INVENTION

Illustrative, non-limiting embodiments of the present invention overcome the aforementioned and other disadvantages associated with related art gas sampling and conditioning systems. Also, the present invention is not required to overcome the disadvantages described above and an illustrative non-limiting embodiment of the present invention may not overcome any of the problems described above.

It is an object of the present invention to provide a novel gas sampling and conditioning system, as well as a method thereof, that overcomes problems associated with conventional sampling and conditioning systems.

It is a further object of this invention to provide a gas sampling thermal conditioner particularly suited for use in hazardous environments that may be integrated with additional structures or in a remote/stand alone configuration.

Further objects of the invention are satisfied by a structure and method for maintaining thermal stability of an extracted gas sample from the source to a remotely situated gas analyzer.

Other objects of the invention are satisfied by a structure and method that provides for purging gas line tubing of air to enhance gas line sample insertion efficiencies.

Still further objects of the invention are satisfied by reducing the inherent risk attendant in hazardous environments and providing a minimal profile while matching or exceeding the performance of larger and more expensive systems.

The present invention also satisfies additional objects by providing structures and methods for gas sample thermal conditioning for analysis with optimized capabilities and minimal cost of operation.

To achieve these and other objects an embodiment in accordance with the invention includes a system for heating a sample of natural gas in a gas transmission line before directing the heated gas into a chromatograph or other analyzer. In accordance with the invention, the system uses only power generated from a cable bundle of a heat tracer.

In brief, a system in accordance with the invention provides a novel gas sample conditioning assembly featuring a combination of a gas line insertion probe and an associated thermal conditioning system for gas sample analyzer input.

As used herein "gas" means any type of gaseous matter capable of pipe transmission, including natural gas, organic gases, industrial gases, medical gases, monomolecular gases, gas mixtures, and equivalents.

As used herein "connected" includes physical, whether direct or indirect, permanently affixed or adjustably mounted. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of specific exemplary embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a novel gas sample thermal stabilizing system and a method thereof for providing significantly augmented efficiencies while mitigating problems of the prior art.

In accordance with one exemplary embodiment, a gas sampling and conditioning system is provided that includes a probe device operable to extract a gas sample from a gas-containing device and a gas conditioning device operable to receive the gas sample from the probe device, wherein the gas conditioning device has one or more components that require electrical power for operation. Further, this exemplary system includes an analyzer device, such as a chromatograph, operable to receive the gas sample from the gas conditioning device and determine constituent components of the gas sample. This exemplary system also includes a first transport device operable to carry gas from the gas conditioning device to the analyzer device, wherein the first transport device is heated by a first heat tracing device that conducts electrical power and generates heat and wherein the one or more components of the gas conditioning device that require electrical power derive the electrical power from the first heat tracing device without requiring an independent power source be provided in addition to the first heat tracing device.

BRIEF DESCRIPTION OF THE DRAWINGS

The aspects of the present invention will become more readily apparent by describing in detail illustrative, non-limiting embodiments thereof with reference to the accompanying drawings, in which.

DETAILED DESCRIPTION OF ILLUSTRATIVE, NON-LIMITING EMBODIMENTS

Exemplary, non-limiting, embodiments of the present invention are discussed in detail below. While specific configurations and dimensions are discussed to provide a clear understanding, it should be understood that the disclosed dimensions and configurations are provided for illustration purposes only. A person skilled in the relevant art will recognize that other dimensions and configurations may be used without departing from the spirit and scope of the invention.

Figure 1:
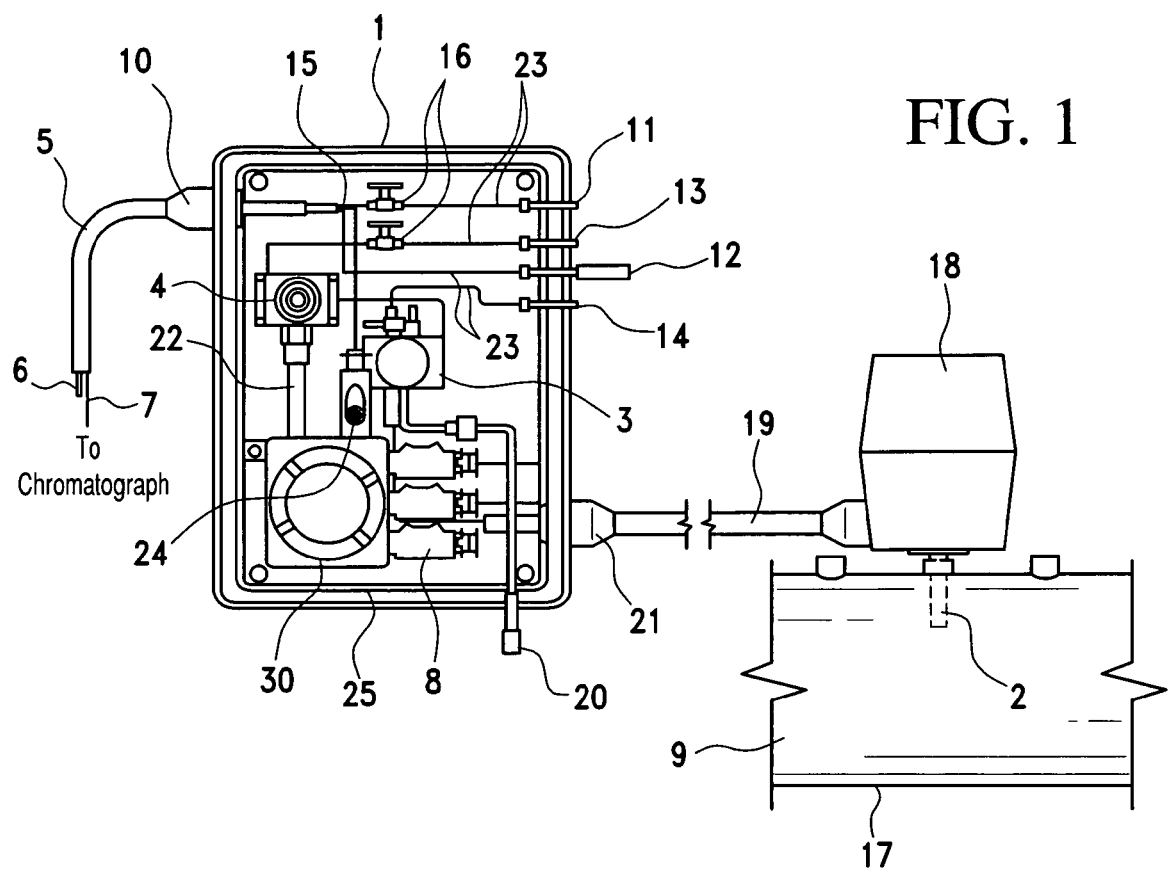
FIG. 1 is diagrammatical partial cut-away front view of the interior of a cabinet connected to a remotely mounted enclosed gas probe according to one exemplary embodiment of the invention.

FIG. 1 illustrates a system in accordance with the present invention. As shown, the system of FIG. 1 comprises a cabinet 1 having, for example, a generally rectangular configuration. The cabinet shown in this embodiment can be composed of polymeric resin, stainless steel, or any other appropriate material or combination of materials, e.g., aluminum panels etc., that provide a substantially strong housing. Further, a cabinet suitable for housing a system in accordance with the present invention is sufficiently commodious to allow for a thick insulating lining, indicated by the dotted line around the inside surface of cabinet 1. For example, to provide sufficient insulation, the insulating lining is approximately 1 inch thick or greater. Cabinet 1 also includes a junction box 30 for receiving and distributing electrical power, a liquid shut-off mechanism 3 to restrict liquid flow, a vaporizing heated pressure regulator 4 to maintain a desired constant gas pressure and an indicator mechanism (not illustrated), such as a series of lights, wired to various connections within the junction box for indicating a status of current operations.

Figure 6A:
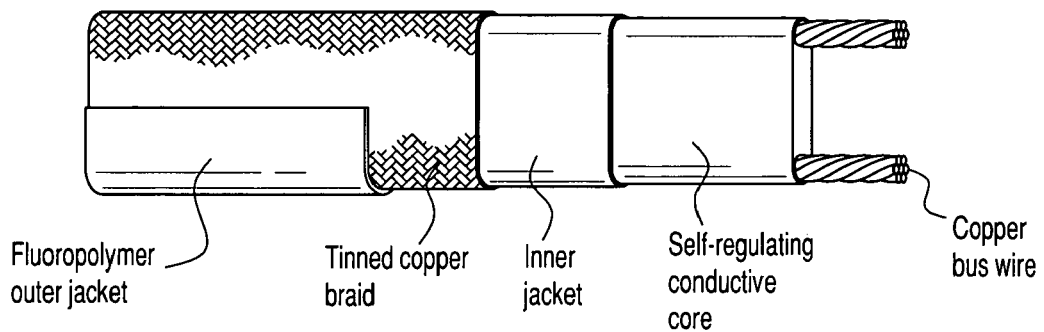
FIGS. 6A and 6B illustrate examples of known heat tracing wire that can be used in accordance with the present invention.
Figure 6B:
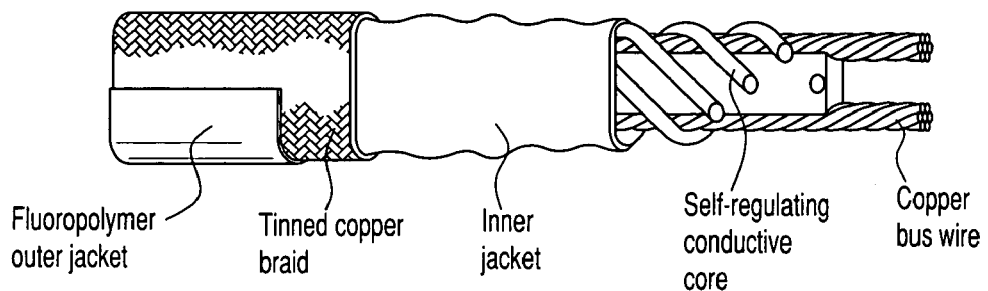
Figure 7:
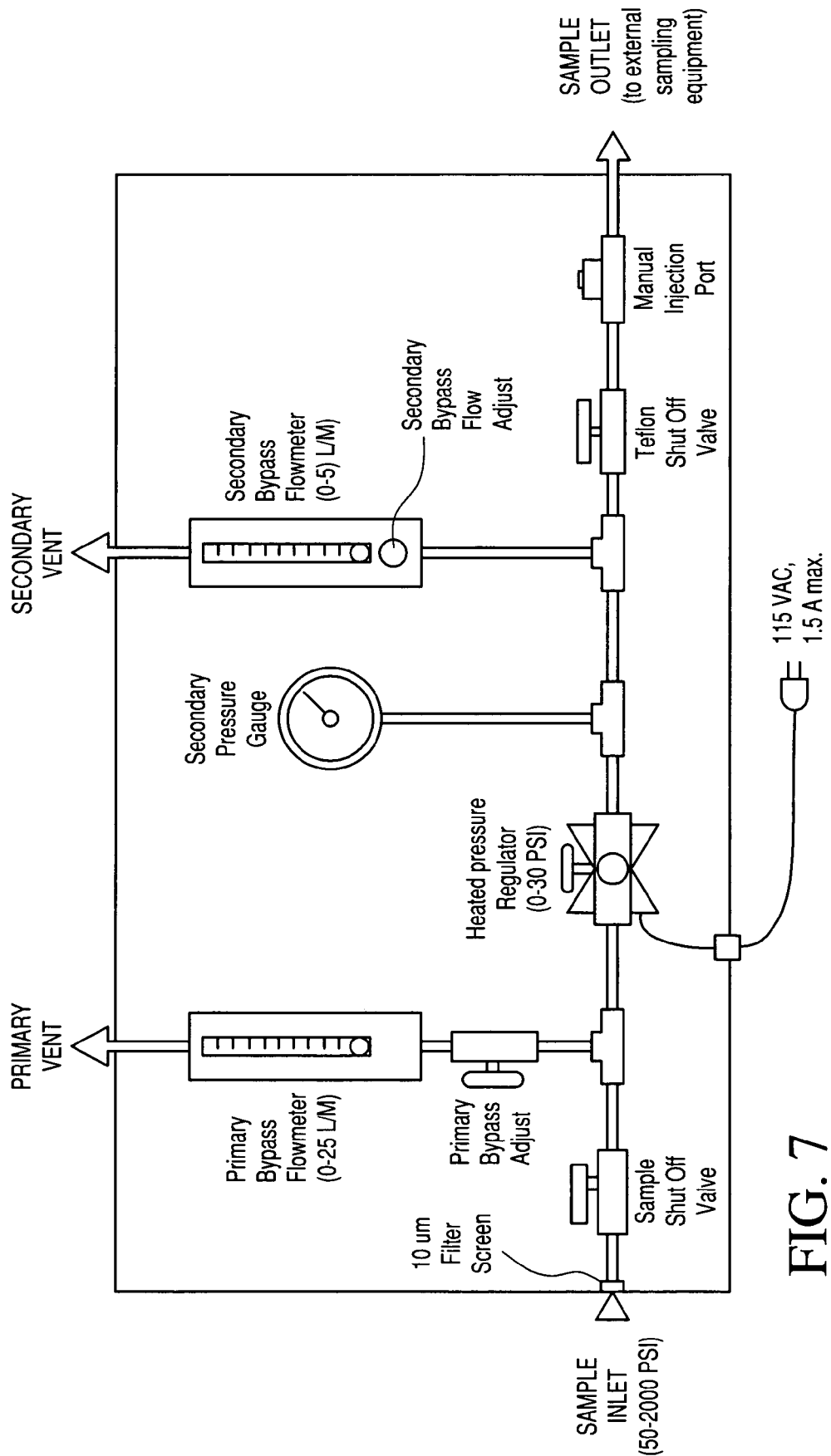
FIG. 7 is a block diagram illustrating a system in accordance with the prior art.

The exemplary embodiment illustrated in FIG. 1 further comprises an inlet/outlet port 10 for accommodating a heated cable bundle 5 which includes a gas line 6 and a power line 7. The power line 7 conducts electrical power, e.g., 110 volts A.C., 220 volts A.C., 12 volts D.C., 24 volts D.C., or any other suitable voltage required by components in or around cabinet 1. According to one embodiment, power line 7 is also a heat tracer cable that generates heat sufficient to maintain the gas within gas line 6 at a temperature above the gas dew point. For example, heat tracer cable 7, which can be self-regulating, can be Raychem heat tracing cable part number 10HBTV1-CT, similar to the heat tracing cables illustrated in FIGS. 6A and 6B.

Additionally, pressure regulator 4 can be, for example, a vaporizing pressure regulator that heats the gas both at its input and at its output. In other words, in order to avoid adverse Joule-Thomson effects, the gas is heated before the pressure is changed, e.g., lowered to a pressure desirable by an analyzer or chromatograph, and the gas is additionally heated after the pressure has been reduced. In this manner the potential for liquid creation due to hydrocarbon dew point dropout is reduced.

In accordance with one embodiment, liquid shutoff mechanism 3 can be a membrane-type device that separates the liquid phase gases from vapor phase gases and provides the liquid phase portion for further processing.

Optionally, an outlet port 11 for expelling heated gases, particularly contaminated heated gases, a pressure relief port 12 for maintaining the pressure within the system below a specified value, and inlet ports 13 and 14 for injecting sample gas for testing purposes, can be provided in cabinet 1.

Gas pipes 23, such as ⅛ inch diameter stainless steel tubing, inside cabinet 1 are for carrying gas from the input port 21 to various selector valves 16 and from the regulator 4 to ports 11–14, discussed above. Wiring 15 shown inside cabinet 1 is the same wiring 7, or at least connected to wiring 7, which is the heat tracer cabling within cable bundle 5 outside cabinet 1. Wiring 15 is routed within cabinet 1 through conduit 24 and into junction box 30 where, for example, the positive polarity and common electrical wires are connected to a terminal board (not shown). Wiring (not shown) within junction box 30 is connected to the terminal board Typical operation of the gas sample and conditioning device described above will now be provided in reference to FIG. 1.

Gas 9, for example natural gas, being transported or otherwise stored within a device, e.g., pipe, 17, is sampled by sample probe 2. For example, sample probe 2 can be a membrane-type gas probe that permits vapor phase gas to permeate through the membrane while preventing liquid phase gases from passing through the probe. Once the sample comprising substantially all vapor phase gas is collected, the sample is directly input to an optional intermediate enclosure device 18 where the sample is heated. For example, the intermediate enclosure device can be a Pony™ device manufactured by Valtronics, Inc., assignee of the present invention. It should be noted that the intermediate enclosure device is optional and according to alternative embodiments of the present invention the intermediate enclosure device is eliminated. In accordance with this embodiment, however, the intermediate enclosure device includes heat tracing cabling which is provided on the interior of the periphery of the enclosure device creating a heated environment within the enclosure and, thus, heating the sample gas. The heat tracing cabling can be similar to the heat tracing devices mentioned above and depicted in FIGS. 8A and 8B.

The heated sample is output from the intermediate enclosure device and transported via a heated cable bundle 19 to an input port 21 of cabinet 1. Heated cable bundle 19 can be the same type of bundle as cable bundle 5 described above. That is, cable bundle 19 can include a stainless steel tube (not shown) through which the sample gas is transported and a heat tracing cable in close proximity to the stainless tube for heating the tube and, thus, the gas within the tube. Around the stainless tube and the heat tracing cable an insulating material and a shielding material, e.g., rubber, plastic, etc., are provided.

The stainless tubing and heat tracing cable enter cabinet 1 via port 21. The stainless tubing is connected to further gas tubing for carrying the sample gas to the liquid separator 3 and the heat tracing cable is connected to a terminal board (not shown) within junction box 30. The heat tracing cable within bundle 19 derives its electrical power from the terminal board within junction box 30.

Within liquid separator 3, any liquid phase gas that is present is separated from the vapor phase gas and is transported via stainless tubing to liquid outlet port 20 for further processing and/or storage. The vapor phase gas is output from liquid separator 3 and is provide to heated vaporizing pressure regulator 4. Regulator 4 heats the inputted gas to within a certain temperature range, e.g., a temperature range determined by the hydrocarbon dew point curve of the particular gas sample, and reduces the pressure of the gas. For example, in the case of natural gas, the inputted pressure could be approximately 2000 psig and the pressure regulator would reduce this pressure to about 10–20 psig, e.g., a desirable pressure range for inputting gas to a chromatograph. Due to the significant pressure reduction in the gas, if the temperature of the gas were kept constant, the joule-thomson effect dictates that hydrocarbon dew point dropout would occur and at least a portion, if not all, of the sample gas would change into its liquid phase. Accordingly, pressure regulator 4 is controlled to heat the reduced-pressure gas to avoid the joule-thomson effect and maintain the sample gas in its vapor phase.

Pressure regulator 4 requires electrical power to generate its heat and, thus, is electrically connected to the terminal board within junction box 30. Specifically, wiring is connected to both the heater elements of regulator 4 and the terminal board of junction box 30 through conduit 22.

The heated vapor phase sample gas is outputted from regulator 4 via additional stainless tubing which is connected to the tubing 6 of cable bundle 5. Optionally, there is provided various valves 16 for controlling the flow of gas through the various stainless tubing 23. For example, sample input port 13 is provided in the event it is desired to pass a sample gas directly through to output port 10, bypassing the liquid separator 3 and regulator 4. In this event, valves 16 would be controlled to prevent gas from traveling from regulator 4 through to output port 10 and only the gas from port 13 would be permitted to flow to port 10. For example, one might want to input a calibration gas into ports 13 or 14 and out port 10 and into tubing 6 in order to confirm that the composition of the gas is not being altered as it passes through the various components of cabinet 1.

Pressure relief port 12 is optionally provided for relieving pressure in the event the pressure at the output of pressure regulator 4 is above the desired range. For example, if the desired range for the output of regulator 4 is 10–20 psig and the output of regulator 4 is 100 psig, pressure relief port 12 would open permitting sample vapor gas to escape outside cabinet 1.

As mentioned above, the output of regulator 4 is connected to port 10 on the inside of cabinet 1 and gas tube 6 from bundle 5 is connected to port 10 on the outside of cabinet 1. The stainless tubes within cabinet 20, including the tube connecting regulator 4 to port 10, are heated along with the other internal components of cabinet 1 by heat tracing cable 25. Heat tracing cable 25 can be, for example, the same type of heat tracing cables as cable 7 within bundle 5, the heat tracing cable within bundle 19 and the heat tracing cable within intermediate enclosure device 18. As shown in FIG. 1, heat tracing cable 25 is provided around the interior of cabinet 1 along the periphery of the outer casing. For example, several loops of heat tracing cable can be made in order to cover a desired portion of the interior surface of the cabinet. Accordingly, because the cabinet is sufficiently insulated, the temperature within cabinet 1 is maintained at a sufficiently high temperature to maintain substantially all of the sample gas within the components of cabinet 1 in the vapor phase.

Heat tracing cable 25 is electrically connected to the terminal board (not shown) within junction box 30. More particularly, cable 25 draws electrical power from the terminal board which, in turn, is electrically connected to heat tracing cable 7 outside of cabinet 1 via a portion 15 which runs from port 10 to the terminal board within box 30.

Because each of the devices within gas conditioning cabinet 1 that require electrical power derive their power from the heat tracing cable that runs in cable bundle 5, there is no need to provide an independent power source to any of the devices within or connected to cabinet 1. For example, each of the heat tracing lines 25, heat tracing lines within cable 19 and heat tracing lines inside enclosure 18 are each powered by the heat tracing line 7 inside bundle 5. Additionally, the heating elements with respect to heated regulator 4 derive their power from heat tracing line 7 as well. Accordingly, a more cost effective and efficient way of conditioning sampled gas is provided.

Because there is an extra load on the heat tracing cable 7, the maximum distance between the analyzer/chromatograph and the conditioning cabinet may be reduced. For example, heat tracing cable 7 might normally maintain a maximum of 150 feet of gas tubing 6 at a temperature between 100–120 degrees F., without the added load of the heating devices in and around cabinet 1. Connecting the added heating elements, e.g., the heat tracing cables and the heated pressure regulator inside the cabinet, etc., might reduce this maximum distance to approximately 130 feet. This issue is easily addressed, however, because, 1) the distance between the analyzer, where the source of the electrical power conducted by heat tracing cable 7 is located, and the conditioning cabinet, is typically well below the maximum distance possible for the given power source to provide sufficient power to the heat tracing cable 7 as well as the additional load of conditioning cabinet 1; and 2) if, for some reason, the original power source is inadequate to provide the necessary electrical requirements, the power source at the location of the analyzer can be switched for one with a higher capacity. For instance, if additional distance is necessary between the analyzer and the conditioning cabinet, and an original 110 volt A.C. source is not sufficient, the 110 volt A.C. source can be exchanged for a 220 volt A.C. source.

Figure 2:
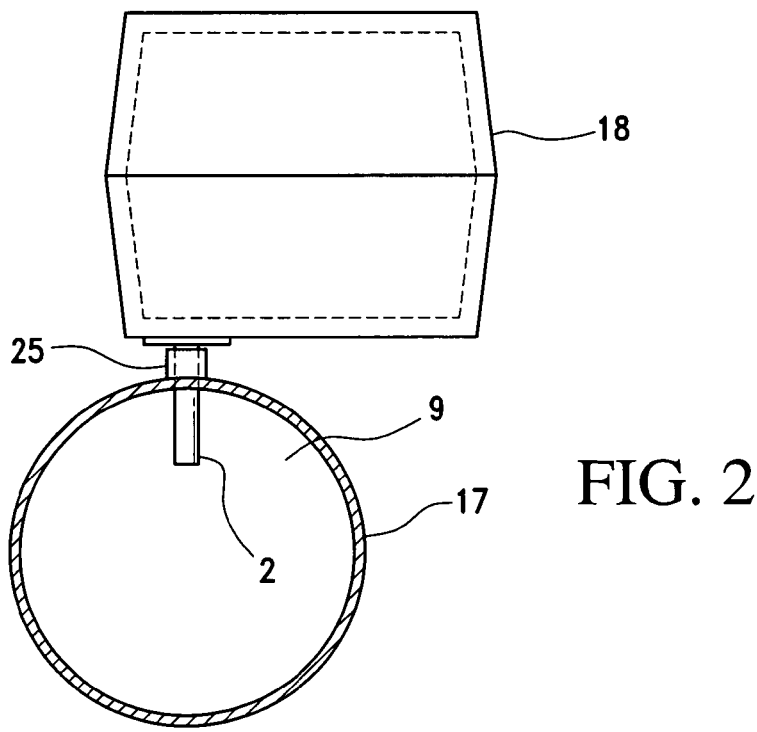
FIG. 2 is a diagrammatical side view of an intermediate enclosure with the remote probe mount in accordance with the embodiment of the invention depicted in FIG. 1.

FIG. 2 is a close-up view of the intermediate enclosure 18 of FIG. 1 with the remote probe 2 attached thereto at the bottom. In accordance with FIG. 2, the viewing angle has been rotated 90 degrees as evidenced by the straight-on view of pipe 17, as opposed to the lengthwise view as shown in FIG. 1. As shown, sample probe 2 enters pipe 17 through sealable port 25 which seals air tight when probe 2 is, removed to prevent escape of gas 9 into the atmosphere and also prevent the atmosphere from contaminating gas 9 within pipe 17.

Figure 3:
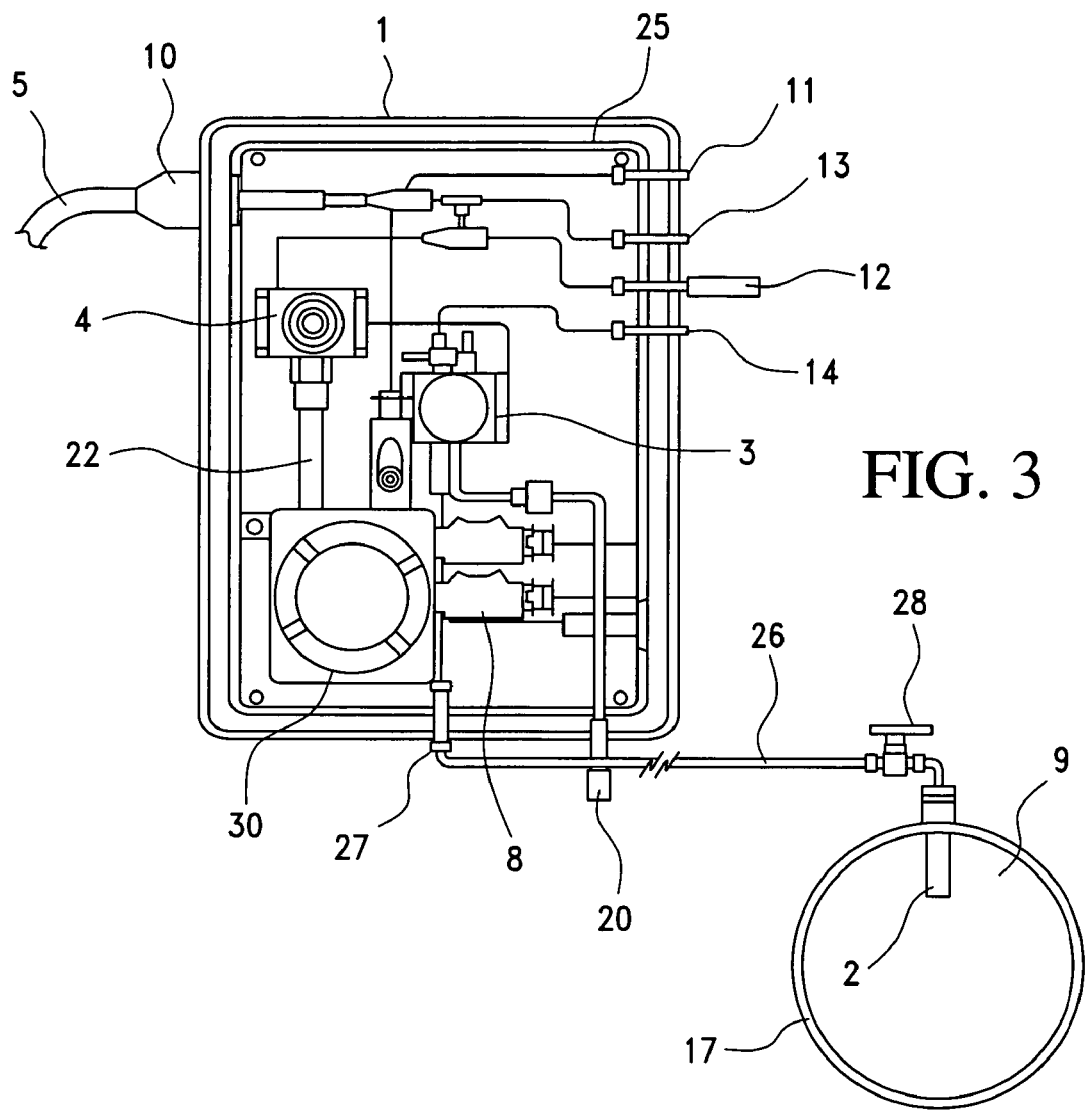
FIG. 3 is a diagrammatical view of a cabinet according to an exemplary alternative embodiment in accordance with the present invention.

FIG. 3 shows an alternative embodiment with respect to the present invention illustrated and discussed in accordance with FIG. 1. Similar devices and components to those which are shown in FIG. 1 are designated with the same reference numbers for sake of consistency. For instance, cabinet 1 and all components within cabinet 1 are the same in the embodiment of FIG. 3 as they are in the embodiment of FIG. 1. One difference between FIG. 3 and FIG. 1 is that the intermediate enclosure device 18 has been eliminated in the embodiment of FIG. 3. In the embodiment of FIG. 3, probe 2 samples the gas 9 within pipe 17 and the gas sample is transported directly to input port 27 of cabinet 1 via gas tubing 26, which may or may not be heated via a heat tracing device (not shown). Valve 28 located close to probe 2 enables shutting off the flow of gas through tube 26 when desired, for example, when probe 2 needs to be replaced.

Figure 4:
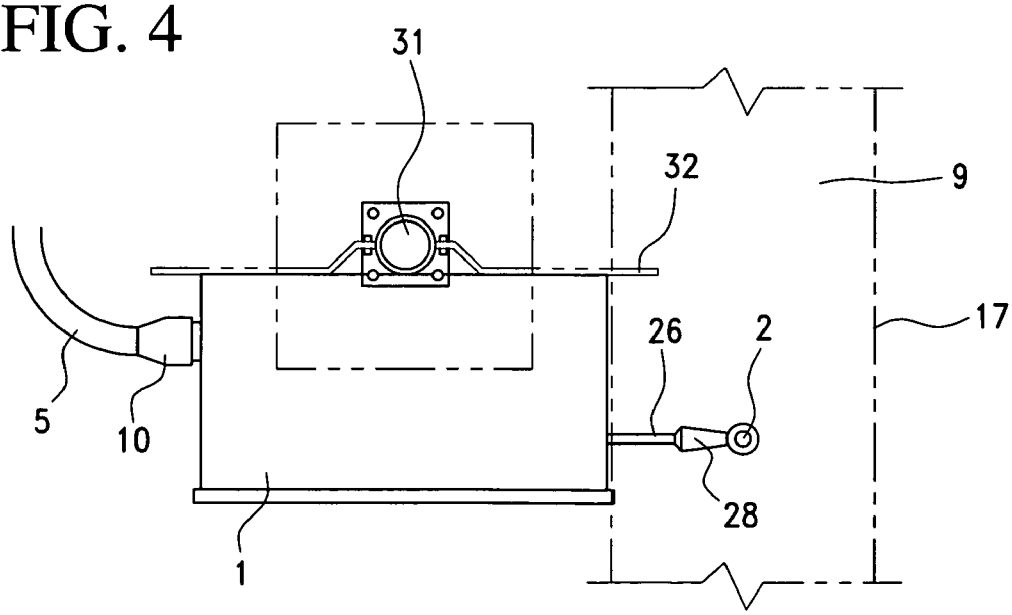
FIG. 4 is a top view of the direct probe close mount embodiment of FIG. 3.

FIG. 4 illustrates a top view of the alternative embodiment of FIG. 3. Like structures are labeled similarly to FIG. 3. In FIG. 4 it is shown that cabinet 1 is ideally mounted, for example, to pole 31 via mounting bracket 32, as close as possible to pipe 17 and probe 2. Accordingly, in the event tubing 26 is not heated, the distance the non-heated gas must travel before entering heated cabinet 1 is minimized, thus, avoiding as much hydrocarbon dew point dropout as possible.

Figure 5:
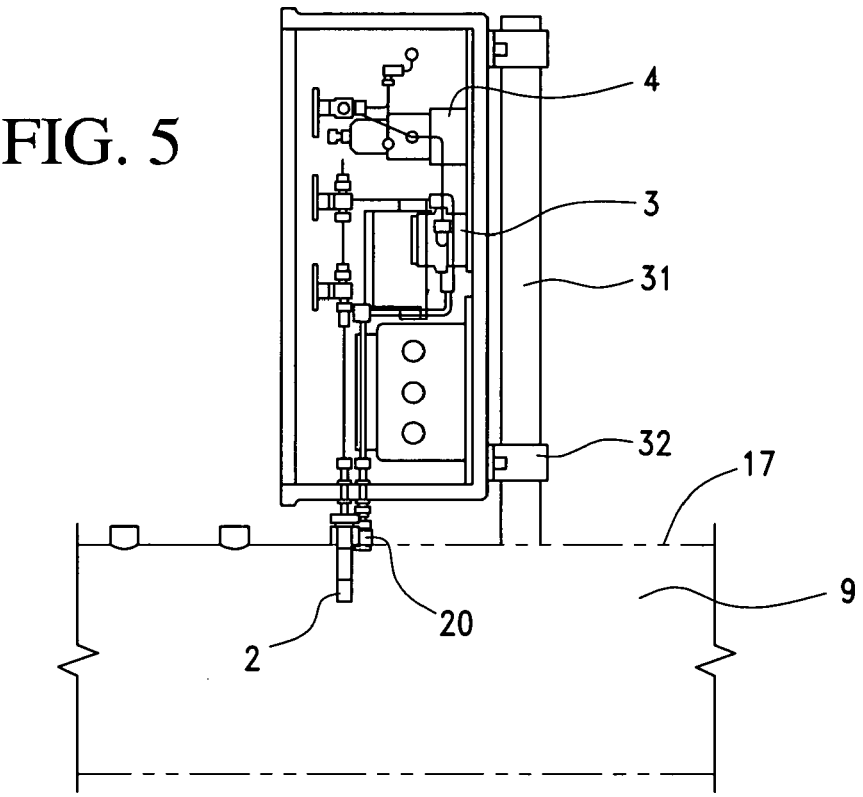
FIG. 5 is a diagrammatical side view of a cabinet according to the close mount embodiment of FIG. 4.

FIG. 5 shows a side view of the close-mount embodiment of FIGS. 3 and 4. Like components are labeled similarly to FIGS. 3 and 4.

Although several embodiments of the invention have been disclosed in the forgoing specification, it is understood by those skilled in the art that many other modifications and embodiments of the invention will come to mind to which the invention pertains, having benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

While various aspects of the present invention have been particularly shown and described with reference to the exemplary, non-limiting, embodiments above, it will be understood by those skilled in the art that various additional aspects and embodiments may be contemplated without departing from the spirit and scope of the present invention It would be understood that a device or method incorporating any of the additional or alternative details mentioned above would fall within the scope of the present invention as determined based upon the claims below and any equivalents thereof.

Other aspects, objects and advantages of the present invention can be obtained from a study of the drawings, the disclosure and the appended claims.

What is claimed is:

1. A gas sampling and conditioning system comprising:
   a probe device operable to extract a gas sample from a gas-containing device;
   a gas conditioning device operable to receive the gas sample from said probe device, wherein said gas conditioning device comprises one or more components requiring electrical power;
   an analyzer device operable to receive the gas sample from said gas conditioning device and determine constituent components of the gas sample;
   a first transport device operable to carry gas from said gas conditioning device to said analyzer device, wherein said first transport device is heated by a first heat tracing device that conducts electrical power and generates heat;
   an intermediate enclosure device operably connected to said probe device, wherein said intermediate enclosure device is for receiving the gas sample from said probe device and heating the gas sample to maintain the gas sample at a substantially constant temperature; and
   a second transport device operable to carry the heated gas sample from said intermediate enclosure device to said gas conditioning device;
   wherein the one or more components of said gas conditioning device that require electrical power derive the electrical power from the first heat tracing device and
   wherein said second transport device comprises a second heat tracing device electrically connected to, and deriving electrical power from, said first heat tracing device.

2. A system as recited in claim 1, wherein said intermediate enclosure device comprises a third heat tracing device integral with or electrically connected to said second heat tracing device.

3. A gas sampling and conditioning system comprising:
a probe device operable to extract a gas sample from a gas-containing device;
a gas conditioning device operable to receive the gas sample from said probe device, wherein said gas conditioning device comprises one or more components requiring electrical power;
an analyzer device operable to receive the gas sample from said gas conditioning device and determine constituent components of the gas sample; and
a first transport device operable to carry gas from said gas conditioning device to said analyzer device, wherein said first transport device is heated by a first heat tracing device that conducts electrical power and generates heat;
wherein the one or more components of said gas conditioning device that require electrical power derive the electrical power from the first heat tracing device;
wherein said gas conditioning device comprises a pressure regulating device operable to heat the gas sample and regulate the pressure of the gas sample to a predetermined pressure value.

4. A system as recited in claim 3, wherein said pressure regulating device is heated and derives electrical power from the first heat tracing device.

5. A system as recited in claim 3, wherein said pressure regulating device reduces the pressure of the gas sample to a value required by said analyzer device and heats the gas sample before and after the pressure is regulated to the predetermined value.

6. A gas sampling and conditioning system comprising:
a probe device operable to extract a gas sample from a gas-containing device;
a gas conditioning device operable to receive the gas sample from said probe device, wherein said gas conditioning device comprises one or more components requiring electrical power;
an analyzer device operable to receive the gas sample from said gas conditioning device and determine constituent components of the gas sample;
a first transport device operable to carry gas from said gas conditioning device to said analyzer device, wherein said first transport device is heated by a first heat tracing device that conducts electrical power and generates heat,
a liquid separator device in communication with said probe device for receiving the gas sample and separating liquid phase constituent components from vapor phase constituent components of the gas sample; and
a pressure regulating device in communication with said liquid separator device and operable to heat the vapor phase gas sample received from said liquid separator device and regulate the pressure of the vapor phase gas sample to a predetermined pressure value;
wherein the one or more components of said gas conditioning device that require electrical power derive the electrical power from the first heat tracing device.

7. A gas sampling and conditioning system comprising:
a probe device operable to extract a gas sample from a gas-containing device;
a gas conditioning device operable to receive the gas sample from said probe device, wherein said gas conditioning device comprises one or more components requiring electrical power;
an analyzer device operable to receive the gas sample from said gas conditioning device and determine constituent components of the gas sample; and
a first transport device operable to carry gas from said gas conditioning device to said analyzer device, wherein said first transport device is heated by a first heat tracing device that conducts electrical power and generates heat;
a junction device electrically connected to the first heat tracing device for distributing electrical power to one or more other devices within said gas conditioning device; and
a heat generating device electrically connected to said junction device for generating heat within said gas conditioning device;
wherein the one or more components of said gas conditioning device that require electrical power derive the electrical power from the first heat tracing device.

8. A method of sampling and conditioning a gas sample comprising: extracting the gas sample from a volume of gas to be conditioned;
separating any liquid phase gas from the vapor phase gas of the gas sample; heating the vapor phase gas to a value within a predetermined temperature range;
regulating the pressure of the vapor phase gas of the gas sample to a value within a predetermined pressure range;
outputting conditioned vapor phase gas within the predetermined temperature and pressure ranges to an analyzer for determination of the constituent components of the conditioned vapor phase gas; and
applying electrical power from a heat tracing device operable to heat the outputted conditioned vapor phase gas to a device in which said heating and pressure regulation are performed.

9. A method as recited in claim 8 further comprising transporting the outputted conditioned vapor phase gas to the analyzer via a device heated by the heat tracing device.

* * * * *